(12) United States Patent
Clark et al.

(10) Patent No.: US 9,421,036 B2
(45) Date of Patent: Aug. 23, 2016

(54) AUTOMATICALLY-DEFLATING, POSTPARTUM TAMPONADE

(71) Applicants: Adam J Clark, Arvada, CO (US); Nathaniel C Moller, Broomfield, CO (US); Anastasia V Borok, San Jose, CA (US); Luke T Jungles, Winston Salem, NC (US); Harshad Sanghvi, Baltimore, MD (US); Jens I Petter, Stavanger (NO)

(72) Inventors: Adam J Clark, Arvada, CO (US); Nathaniel C Moller, Broomfield, CO (US); Anastasia V Borok, San Jose, CA (US); Luke T Jungles, Winston Salem, NC (US); Harshad Sanghvi, Baltimore, MD (US); Jens I Petter, Stavanger (NO)

(73) Assignee: Jhpiego Corporation, Baltimore, MD (US)

( * ) Notice: Subject to any disclaimer, the term of this patent is extended or adjusted under 35 U.S.C. 154(b) by 446 days.

(21) Appl. No.: 13/859,691

(22) Filed: Apr. 9, 2013

(65) Prior Publication Data
US 2014/0303747 A1 Oct. 9, 2014

Related U.S. Application Data

(60) Provisional application No. 61/621,543, filed on Apr. 8, 2012.

(51) Int. Cl.
*A61M 29/00* (2006.01)
*A61B 17/42* (2006.01)
*A61B 17/12* (2006.01)
*A61B 17/00* (2006.01)

(52) U.S. Cl.
CPC ....... *A61B 17/42* (2013.01); *A61B 2017/00557* (2013.01); *A61B 2017/12004* (2013.01); *A61B 2017/4216* (2013.01)

(58) Field of Classification Search
CPC .................... A61M 29/02; A61M 2210/1433; A61M 25/10; A61B 17/42; A61B 2017/00557
USPC ......................................... 606/191, 192, 193
See application file for complete search history.

(56) References Cited

U.S. PATENT DOCUMENTS

| | | | |
|---|---|---|---|
| 6,676,680 B1 | 1/2004 | Packer | |
| 8,123,773 B1 | 2/2012 | Shirley | |
| 2001/0007945 A1* | 7/2001 | Piraka | A61M 25/10 606/193 |
| 2004/0030352 A1 | 2/2004 | McGloughlin et al. | |

(Continued)

OTHER PUBLICATIONS

Dabelea, V. et al. "Intrauterine balloon Tamponade in the management of postpartum hemorrhage", Am J Perinatol (Jun. 13, 2007), vol. 24, No. 6, pp. 359-364.

(Continued)

*Primary Examiner* — Tuan V Nguyen
*Assistant Examiner* — Kevin Everage
(74) *Attorney, Agent, or Firm* — Larry J. Guffey

(57) ABSTRACT

An improved device for the management of a patient's uterine hemorrhage has improvements that include: (a) an inlet valve for controlling the flow of fluid into an expandable vessel, (b) an adapter having a free end and a connection end that connects to the third opening in a tube that has openings at each of its ends, (d) a pressure release component that connects to the adapter's free end and provides for the automatic release of a quantity of fluid sufficient to maintain an approximate, steady state, uniform operating pressure within the device, and (e) an attachment means that affixes the free end of the expandable vessel to the tube at a point that is distal from a tube end so that a portion of the tube extends into the expandable vessel and can be used as a core to assist with the placement of the vessel into the patient's uterine cavity prior to its inflation.

8 Claims, 7 Drawing Sheets

(56) References Cited

U.S. PATENT DOCUMENTS

| | | | | |
|---|---|---|---|---|
| 2006/0173486 A1* | 8/2006 | Burke | ............. | A61B 17/12099 606/193 |
| 2010/0082057 A1* | 4/2010 | Borkon | ................ | A61M 29/02 606/193 |

OTHER PUBLICATIONS

Miller, S., et al. "Prevention and treatment of postpartum hemorrhage: new advances for low-resource settings", J Midwifery Womens Health (Jul. 2004), vol. 49, No. 4, pp. 283-292.

Doumouchtsis, S. et al. "Management of postpartum hemorrhage by uterine balloon tamponade: Prospective evaluation of effectiveness", Acta Obstetricia et Gynecologica (Aug. 2008), vol. 87, No. 8, pp. 849-855.

Doumouchtsis, S. et al. "Systematic review of conservative management of postpartum hemorrhage: what to do when medical treatment fails", Obstetrical and Gynecological Survey (Aug. 2007), vol. 62, No. 8, pp. 540-547.

Haq, H. et al. "Control of Postpartum and Post Abortal Haemorrhage with uterine packing", JPMA (Sep. 2005), vol. 55, No. 9, pp. 369-371.

Manoogian, S. et al. "Dynamic material properties of the pregnant human uterus", Journal of Biomechanics (Apr. 25, 2012), vol. 45, No. 9, pp. 1724-1727.

\* cited by examiner

56a

56b

56c

56d

56e

56f

AUTOMATICALLY-DEFLATING, POSTPARTUM TAMPONADE

CROSS-REFERENCE TO RELATED APPLICATION

This application claims the benefit of U.S. Provisional Patent Application No. 61/621,543, filed Apr. 9, 2012 by the present inventors and having the same title as the present application. The teachings of this earlier application are incorporated herein by reference to the extent that they do not conflict with the teachings herein.

BACKGROUND OF THE INVENTION

1. Field of the Invention

The present invention relates generally to a device for treating postpartum mothers. More particularly, the present invention relates to a low-cost device for treating postpartum hemorrhaging.

2. Description of the Related Art

Postpartum hemorrhage (PPH) is the leading cause of maternal mortality worldwide. There are over 14 million cases of PPH every year, and approximately 150 thousand of those cases end in death. The majority of these deaths occur in resource-constrained settings, with an estimated half occurring in sub-Saharan Africa and a third in South Asia. Additionally, there are over 20 million women living with chronic illnesses, such as anemia, which result from PPH. Moreover, a child is ten times more likely to die before a second birthday if the mother dies from PPH.

PPH is defined as the loss of ≥500 ml of blood within twenty four hours after the birth of a child. PPH arises due to complications during the third and fourth stages of labor. The main cause of PPH is uterine atony, which accounts for up to 80% of the cases. Additional causes include retained placenta, genital tract trauma, and bleeding disorders.

PPH is largely manageable with access to adequate resources. However, in developing nations with their often, resource-constrained, medical facilities, PPH is much more devastating. The nearest referral hospital in such nations can often be many hours away from a birthing mother—this can result in a potentially dangerous situation when one considers that it can take less than two hours for a woman to bleed to death from a PPH. Additionally, the screening of at-risk women for earlier referrals to nearby hospitals is challenging because two-thirds of pregnant women display no risk factors for PPH.

There are a number of commercially available medical devices available for treating a woman who is suffering from a PPH. Most of these function by trying to stop or prevent bleeding by applying pressure on a women's uterine wall which is the likely location or source of bleeding. This pressure applying step is typically accomplished by inserting an un-inflated balloon tamponade into the uterus and then inflating it with a saline solution. The volume of the saline fill is pre-determined using ultrasound, or is achieved incrementally with observations for bleeding in between each aliquot to determine if a sufficient volume has been added in an attempt to apply pressure to the source of the PPH and thereby stop it.

Examples of these commercially available devices include the "Bakri SOS Postpartum Balloon (Bakri)" (available from Cook Medical), the "Sengstaken-Blakemore Oesophageal Balloon (S-B)," the "Balloon Tamponade Catheter (BT-Cath)" (available from Utah Medical), the "Rusch Hydrostatic Catheter Balloon (HCB)," and the "Belfort-Dildy Obstetric Tamponade (B-D)" (available from Glenveigh Medical).

All of these devices share the distinction of being comparatively costly and therefore prohibitively expensive for use in developing countries where medical device cost considerations can often be paramount. Except for the HCB device, they all also share the characteristics of being comparatively complicated to use and non-reusable; plus they have maximum fill capacities of only about 500 ml which is substantially less than the typical volume of the entire uterine cavity (i.e., up to 1800 ml).

Uncertainty around the proper fill volume and the variability from woman to woman is reported to be the cause of the major reason why these devices fail—i.e., insufficient inflation volumes allow them, when in service, to slip downward and fall out of a patient's uterus. To prevent this occurrence, additional saline volumes are added to the balloon and/or gauze packing is often used to hold these devices in place. However, significant health risks can arise from this practice, including the concealment of ongoing bleeding.

Furthermore, the Bakri device has the disadvantage of being time-consuming to fill, as its recommended use entails utilizing ultrasound to estimate the volume of the uterus prior to filling the device. Meanwhile the S-B and HCB devices were not designed to be used in addressing PPH situations and they require some on-site modifications prior to their use for such purposes. Many health practitioners are reportedly not comfortable with such other-than-intended-use applications; this has apparently limited these devices' use in PPH situations.

There is an innovated-out-of-necessity, cost-effective alternative to these commercial devices. It is an "Improvised Condom Tamponade (ICT)" device that uses a condom tied to an inexpensive catheter to create a device for managing PPH.

Additionally, there are reportedly research development programs that are directed towards developing an alternative, low-cost, balloon tamponade device for use in managing PPH cases in developing countries. These include the single-use, balloon-included "Uterine Balloon Tamponade (UBT)" (which is under development by the non-profit PATH) and the condom-using "Tampostat" (which is under development by Jibon Health Technologies).

Further disclosures regarding the state of the technology in the field of the present invention are also found in various patent documents. See, e.g., U.S. Pat. Nos. 8,123,773 and 6,676,680, and USPAP 2004/0030352.

Thus, despite the existence of significant technology and commercially available devices for addressing PPH situations, we see that, because of the various problems with many of these devices, there is still a need for the development of improved devices which can help address PPH and other uterine wall bleeding situations.

SUMMARY OF THE INVENTION

Recognizing the need for the development of an improved device for the management of a patient's uterine hemorrhage, the present invention is generally directed to fulfilling this need.

According to the present invention, the improvements to a device (of the type having a tube with a lumen that extends between the tube's ends and wherein each of these ends has an opening that connects with the lumen, and wherein the tube's outer surface proximate one of its ends is configured to allow for the free end of an expandable vessel (e.g., a balloon or condom), which is supplied by a health care worker using the device, to be connected to this end in order to allow for the vessel to be inflated with a pump mechanism, which is also supplied by the health care worker using the device, until a portion of the inflating outer surface of the vessel expands to apply a pressure along a portion of the patient's uterine cavity) for the management of a patient's uterine hemorrhage include: (a) a one-way, inlet valve connected to a tube end for controlling the flow of fluid into the expandable vessel, (b) wherein the lumen also has a third opening located between its ends, (c) an adapter having a free end and a connection end and a passage that extends between these ends, and this adapter having a configuration adapted to allow for the connection end to be connected to the lumen's third opening, (d) a pressure release component having a configuration adapted to connect to the adapter's free end and provide for the automatic release from the device of a quantity of fluid sufficient to maintain an approximate, steady state, uniform operating pressure of the fluid within the device, and (e) an attachment means having a configuration adapted to affix the free end of the expandable vessel to the tube outer surface at a point that is distal from a tube end a distance, L, so that a portion of the tube extends into the expandable vessel and can be used as a core and guide to assist with the placement of the vessel into the patient's uterine cavity prior to the inflation of the vessel.

The improvements to this device may also include: (f) selecting the diameter and material of fabrication of the tube so as to aid in allowing the portion of the tube that extends into the expandable vessel to serve as a core and guide in the placement of the vessel into a patient's uterine cavity, (g) the pressure release component configuration further adapted to allow for the steady state operating pressure in the device to be in the range of 0.5-4.5 psi and to automatically allow for the release of fluid from the device so that the steady state operating pressure in the device is controlled to within the range of 5%-30% of its steady state operating pressure, and (h) fixing the distance, L, that a portion of said tube extends into the expandable vessel, is in the range of 4-8 inches.

Thus, there has been summarized above (rather broadly and understanding that there are other preferred embodiments which have not been summarized above) the present invention in order that the detailed description that follows may be better understood and appreciated.

BRIEF DESCRIPTION OF THE DRAWINGS

The accompanying drawings provide visual representations which will be used to more fully describe the representative embodiments disclosed herein and can be used by those skilled in the art to better understand the present invention and its inherent advantages. In these drawings, like reference numerals identify corresponding elements and.

DESCRIPTION OF THE PREFERRED EMBODIMENT

Figure 1:
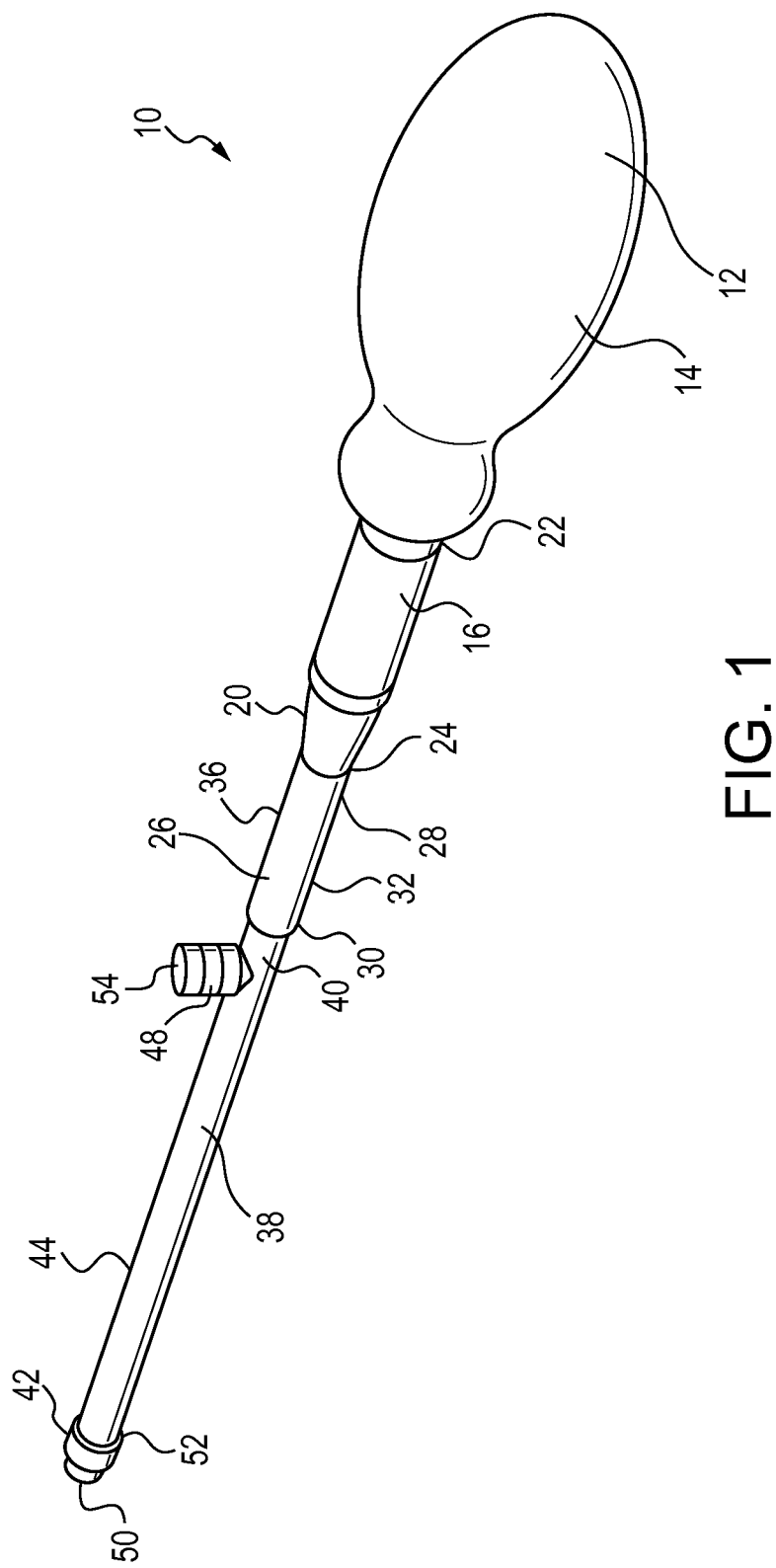
FIG. 1 illustrates a perspective view of a first configuration for the automatically-deflating, postpartum tamponade of the present invention.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The presently disclosed subject matter now will be described more fully hereinafter with reference to the accompanying Drawings, in which some, but not all embodiments of the inventions are shown. Like reference numbers introduce in describing the various elements of the invention refer to same elements throughout this following discussion.

An embodiment in accordance with the present invention provides a device for management of postpartum hemorrhage (PPH) and other situations in which there is bleeding from a patient's uterine cavity. The present invention includes an expandable vessel configured for insertion and inflation within a uterus. This vessel is inflatable with air or any other biocompatible fluid that is suitable for use in such a medical procedure. The present invention also includes a one-way check valve for use in inflating this vessel and a pressure release component for releasing the fluid used to inflate the vessel. This pressure release component is set to automatically release the fluid within the device when the pressure when the device exceeds a critical value. This critical value is defined such that the pressure applied is high enough to be clinically effective in achieving the tamponade technique, while also low enough to mitigate safety risks (e.g. distention of the uterus). If there is an increase in pressure in the device (for instance, due to adding more fluid to the device or the occurrence of contractions of a patient's uterus), the pressure release component will activate and relieve this additional pressure.

Figure 2:
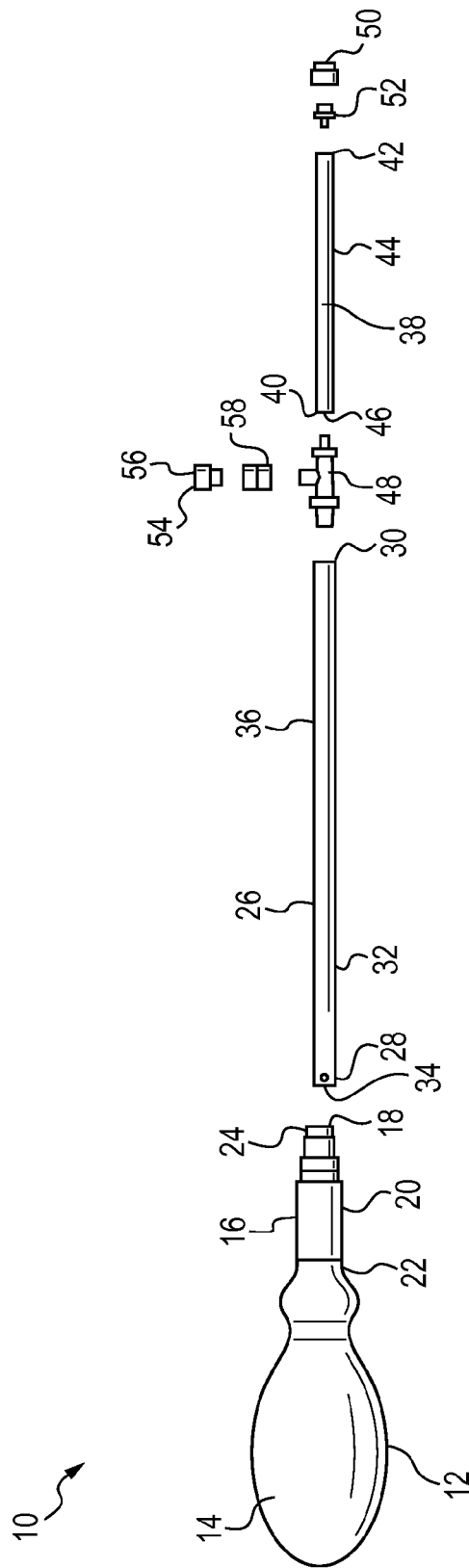
FIG. 2 illustrates an exploded view of the automatically-deflating, postpartum tamponade illustrated in FIG. 1.

FIGS. 1 and 2 illustrate a perspective and an exploded view, respectively, of the first of a number of configurations that are suitable for the present invention, an automatically-deflating postpartum tamponade, 10. This first configuration includes an expandable vessel or balloon 12, which is configured to be insertable into and inflatable within a uterus. The balloon 12 includes an inflatable bulb 14 and a coupling region 16 that has a defined axial length, L. The coupling region 16 terminates in opening 18 defined by an outer wall 20 of the balloon 12. This opening 18 is configured such that fluid can travel though it as the bulb 14 of the balloon 12 inflates. Generally speaking, the coupling region 16 has a first end 22 and a second end 24, wherein the diameter of the coupling region 16 decreases from the first end 22 to the second end 24.

The balloon 12, illustrated in FIGS. 1 and 2, can be manufactured using a dip molding process and will be made from a rubbery or flexible material, such as a biocompatible latex or silicone. Preferably, the balloon 12 is made from a material with a hardness that is measured on a durometer scale in a range of 50 A to 100 A and an elasticity such that a segment of it can be stretched to a length that is on the order of 500% to 800% of its original length. However, any suitable material with a hardness and/or flexibility known to one of skill in the art can be used. The dip molding process allows the production of high volumes of the device at a low price, but any other known method of forming the balloon 12 could also be used.

As an alternative to this carefully manufactured and somewhat costly balloon, the present invention can also exist in a form that does not provide such a balloon—but instead allows the health care workers who will be using the present invention to substitute a low-cost alternative to this balloon. A suitable choice for this alternative is a condom 12a or other suitable and appropriately scaled, inflatable vessel, e.g., a surgical glove. See FIG. 3.

Figure 3:
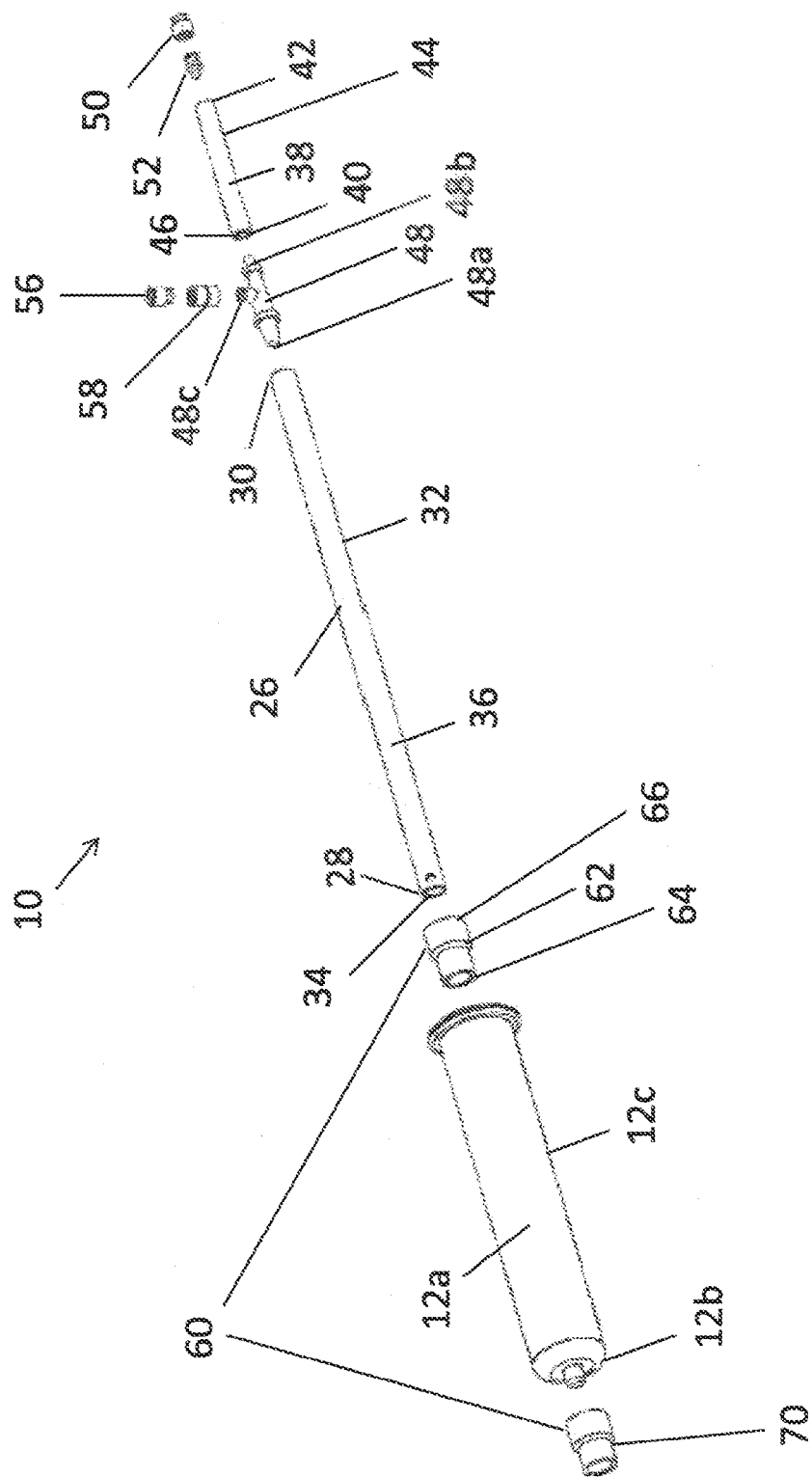
FIG. 3 illustrates a perspective view of a second configuration, wherein a condom is used instead of an especially manufactured balloon, for the automatically-deflating, postpartum tamponade of the present invention.

As illustrated in FIGS. 1-3, the present invention 10 also includes a large diameter tube 26 having a first end 28 and a second end 30 and an outer wall 32 defining an elongate passage or lumen 34 extending between openings in each of these ends 28, 30. When the present invention 10 is assembled, the first end 28 of the large diameter tube 26 is disposed within the balloon 12, such that the balloon's coupling region 16 extends over the outer surface 36 of the large diameter tube 26 so that a segment of this tube of length L extends into the balloon. The large diameter tube 26 is thereby used as a core and guide for the un-inflated balloon 12 to give it the rigidity necessary to insert the balloon into a patient's anatomy. This large diameter tube 26 can be made from any biocompatible and somewhat rigid material known to one of skill in the art. The diameter and material of fabrication of this tube is selected so as to aid in allowing the portion of the tube that extends into the balloon or condom to serve as a core and guide in the placement of the un-inflated balloon into the uterine cavity of the patient prior to the inflation of the balloon.

Experimentation has shown that the length L is not that critical due to the great elasticity of the condom (i.e., can expand to a volume of 20 liters). Thus, the length L could conceivably be almost negligible. However, for the tube use as a core to help place the balloon into a patient's uterus, we have found that a length L in the range of 4-8 inches is most useful.

When a carefully manufactured balloon is used with the present invention, the large diameter tubing 26 is attached to it 12 using mechanical or chemical bonding. Adhesive, heat, and chemical bonding agents, such as cyclohexanone, may be used to secure connections between the tubing and the balloon, as well as between any other tubing and adapters or plastic to plastic bonds described herein. Any other means known to one of skill in the art can also be used.

When a condom 12a is used with the present invention, an attachment means 60 is used to mechanically attach or connect it to the large diameter tubing 26. This connection is secure enough to withstand the pressure within the present invention without leaking.

As previously mentioned, there are other similar devices under development which utilize condoms rather than carefully manufactured balloons. The methods that these other devices used to attach their condoms include using a suture or perhaps even using two condoms to try to avoid leaks. However, in our development efforts, we found that such attachment methods could be very difficult to perform with the tube to which the condom is being attached is slippery and when the one trying to accomplish this attachment is wearing surgical gloves and under adverse conditions (e.g., surfaces are covered in blood and this is an emergent situation with the woman continuing to bleed and emotions and adrenaline running high).

To overcome these attachment problems, the present invention utilizes an attachment means 60. A first attachment member 62 is slid down over the first end 28 of the larger diameter tube 32 so that it is located at an axial distance of L from the tube's first end 28.

Figure 4:
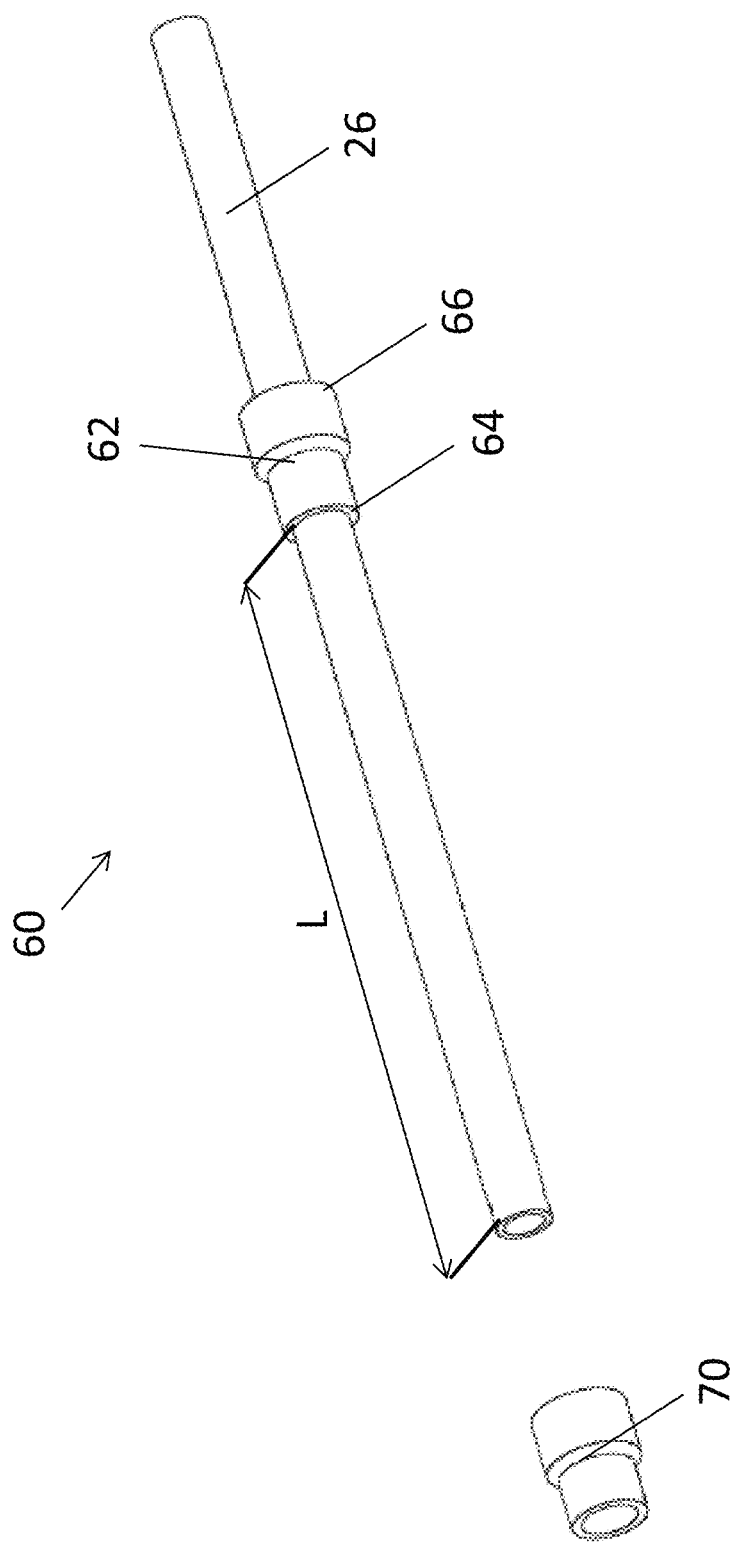
FIG. 4 illustrates a perspective view of the condom attachment means of the present invention.

Then, the condom is unrolled onto the tube 32 and down beyond the distal end 64 of the first attachment member. A second attachment member 70 is next slid over the end of the tube 32 which has the condom 12a already rolled out onto it. Next, the second attachment member 70 is slid down onto the first attachment member 62, with the condom trapped between the two attachment members. Finally, the distal end 64 of the first attachment member is turned upward and back onto itself, along with the free end 12b of the condom which lies above it 64, so that one has two, overlapping layers of the condom's outer surface 12c and this turned upward and backward portion of the first attachment member's distal end 64, i.e., it's lip portion 66, lying above the distal end of the second attachment member 70, see FIG. 4, and thereby securing the condom in place. These attachment members, especially the first attachment member with its very flexible lip portion 66 can be formed from any biocompatible material with appropriate flexibility known to one of skill in the art.

An alternative to this attachment means is a single-member attachment mechanism similar to a hose clamp 80 that secure the condom to the tube 32. See FIG. 5. However, note that both of these alternative attachment means utilize a mechanical interference fit to achieve their attachment of the condom to the tube.

The present invention 10 also includes a small diameter tube 38, which is used in the portion of the present invention that remains external to the patient. This small diameter tube 38 is less obtrusive and easier to manage and conceal in instances when the device is left in place within the patient for an extended period of time. The small diameter tube 38 has a first end 40 and a second end 42 and an outer wall 44 defining an elongate passage or lumen 46 that extends between openings in each of the tube's ends. This small diameter tube 38 can be formed from any biocompatible material with appropriate flexibility known to one of skill in the art.

As seen in FIGS. 1 and 2, this small diameter tube 38 is coupled to the large diameter tube 26 using an adapter 48 which has a first opening 48a that couples to the second end 30 of the large diameter tube and a second opening 48b that connects to the first end 40 of the small diameter tube. The adapter 48 is configured such that fluid can flow through it from the small diameter tube 38 to the large diameter tube 26 and vice versa. The adapter 48 also has a third opening 48c that provides an attachment site for a pressure release or relief component 56.

Alternately, the large diameter tube 26 and the small diameter tube 38 can be formed together to yield a single tube with a graded reduction in diameter between the two tubes and a third opening in the resulting tube's lumen that is appropriately situated between the tube's opposing ends so as to provide for the adapter's necessary third opening or connection end that provides an opening to the tube's lumen and this adapter's consequent free end that acts as a coupling point for entry via the passage between these free and connection ends to the device's pressure controlled cavity consisting of the lumen and the inflated balloon.

A one-way, inlet check valve 50 is used to control fluid input into the present invention 10. This fluid can be air or any other suitable fluid known to one of skill in the art. The one-way, inlet check valve 50 is coupled to the second end 42 of the small diameter tube 38 with a standard barb to luer-tapered, female coupling or fitting 52. Alternately, the one-way, inlet check valve 50 can be manufactured with a barbed connection, such that this fitting 52 is not necessary. Any other suitable means for attaching the one-way, inlet check valve 50 to the present invention can also be used. The one-way, inlet check valve 50 is set to a comparatively low cracking pressure (e.g., 0.2 psi) to increase the valve's ease of use.

The means for releasing fluid from the present invention includes a pressure release component 56 which has an opening 54 to the surrounding atmosphere and a straight connector 58 that can be attached to the adapter's third opening 48c. Alternately, the pressure release component 56 can be manufactured with an adapter 48 already built into it 56.

This pressure release component 56 automatically allows the release of fluid as force is naturally applied by a patient's uterus onto the balloon of the present invention that is inserted and inflated therein. The pressure release component 56 is set to open at a value that mitigates the risks of higher pressures (e.g. distention of the uterus) by activating when the pressure in the system increases (e.g. due to additional inflation and/or uterine contractions of the patient) beyond a certain percentage of it established, steady state (i.e., as opposed to during inflation and deflation), operating pressure. This allows for the management of bleeding, but also allows the uterus to expel fluid from the balloon or condom as the uterus naturally contracts.

It should be noted that the pressure relief component of the present invention is a key element of the present invention. The ability to make such a component only became a possibility due to the recent advancements in our knowledge regarding our knowledge of the pressures being experienced in the uterus during labor. See FIG. 5 for an idealized plot of the temporal variations of pressure that are expected in the present invention. This data was used in the creation of the pressure release component 56 of the present invention.

This plot shows the ideal filling, dwell, and deflation pressure curve over time. As the balloon or condom of the present invention is initially filled, there is seen to be very little pressure in this vessel. During the inflation period there is an inflection point in the curve that corresponds to the beginning of the inflation of the condom. The value of this invention's critical operating pressure is only reached once full contact is made between the inflated condom and the uterus. Any further significant increases beyond this operating pressure will cause an activation of the invention's pressure relief component so as to allow fluid to escape from the invention thereby lowering the pressure in the balloon or condom.

Figure 5:
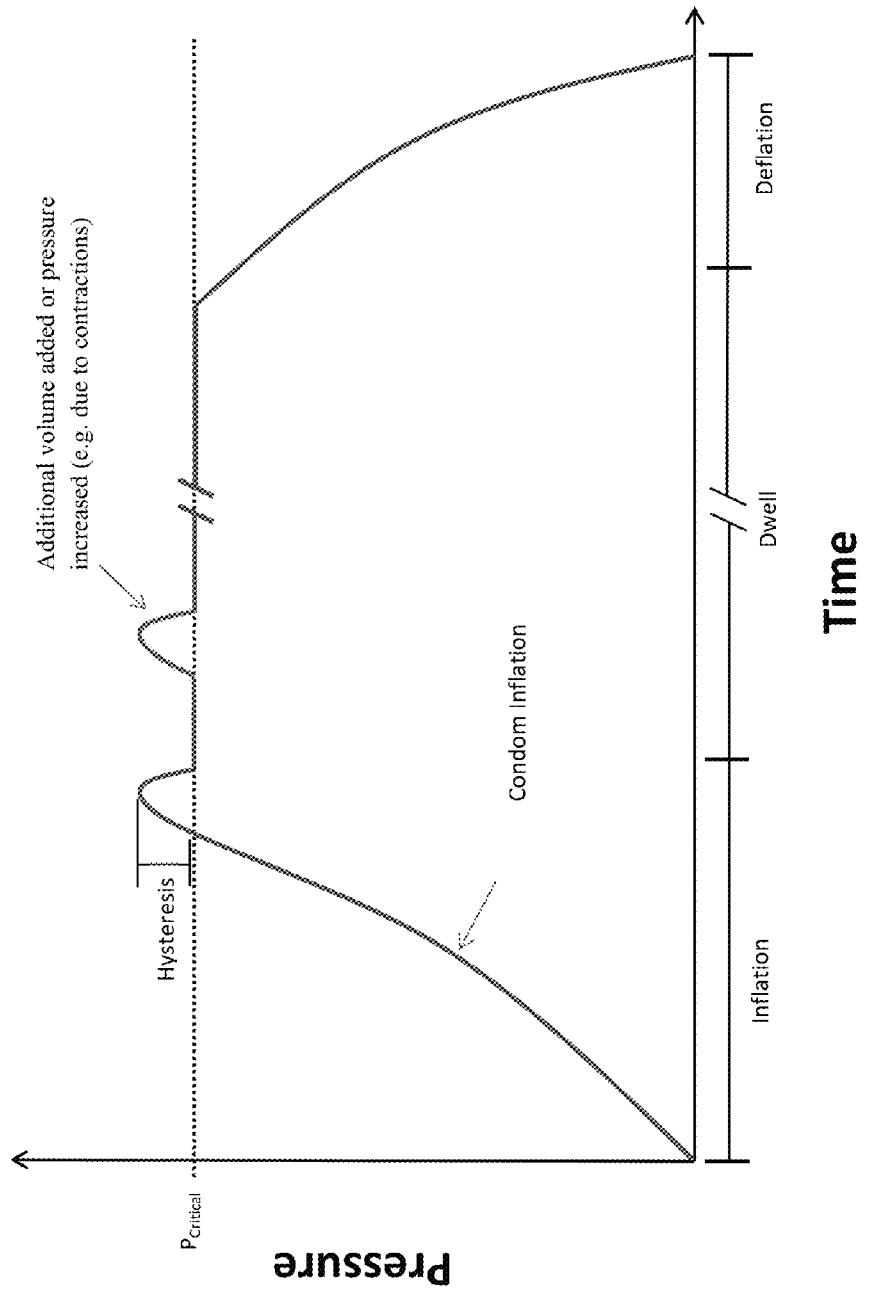
FIG. 5 shows a plot of the temporal variations of the pressures expected to be experienced in the present invention.

Likewise, any additional volume of fluid added to the invention or any increases in pressure (e.g. due to uterine contractions) will cause the vessel's pressure to rise, thus activating the pressure relief component again. Activation of this pressure relief component may also serve as a feedback mechanism to the user that sufficient volume has been added or that the uterus is contracting. The dwell period is a very long period (~24 hours) and thus the time scale on FIG. 5 is not shown to scale, but condensed in parts to allow a representation to be given for the pressure variations during contractions, inflation and deflation.

Typical operating pressures for the present invention are expected to be in the range of 0.5-3.5 psi+/−5% to 30%. The lower end of the range is defined by what is clinically effective and the upper limit of the range is defined by what is clinically safe. The upper limit of 3.5 psi as used here is based on the article: Sarah J. Manoogian et. al., "Dynamic Material Properties Of The Pregnant Human Uterus," *Journal of Biomechanics* 45 (2012), pp 1724-1727. The teachings of this article are herein incorporated into this application by reference.

The typical temporal variations in pressure that are expected to be experienced by the present invention are very difficult to estimate. Significant research continues on this point. The pressure release component of the present invention has been initially configured so that it is operable based on pressure fluctuations of 5% to 30% about mean operating pressures in the range of 0.5-4.5 psi.

When the present invention is of the form that does not include an inflatable vessel, it is a device that is open to the surrounding atmosphere via the opening in the larger diameter tube's first end. However, when the condom or balloon is secured this end, it becomes a closed, pressure controllable device. Once the device is closed, fluid can be input into it until the pressure within the device reaches a desired operating level that corresponds to the condom being fully inflated such that its outer wall places a uniform pressure on the uterine wall of the patient into whom the balloon has been inserted. The patient's subsequent uterine contractions will cause the pressure inside the device to increase, but only up to an allowed, maximum pressure which is set by the setting on the present inventions' pressure relief component 56.

Once the condom or balloon is attached and the device is inflated, its pressure relief component 56 becomes a critical component for the safety and performance of the present invention. This is why the present inventors have dedicated so much effort to the development of this pressure relief component.

Figure 6:
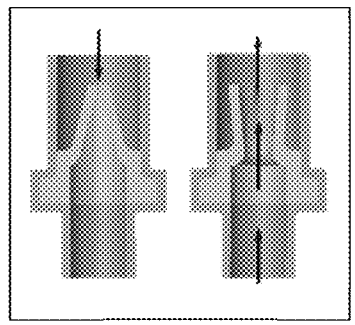
FIG. 6 illustrates a perspective view of some of the alternative components that can go into creating an OEM version of the pressure relief component of the present invention.
Figure 6:
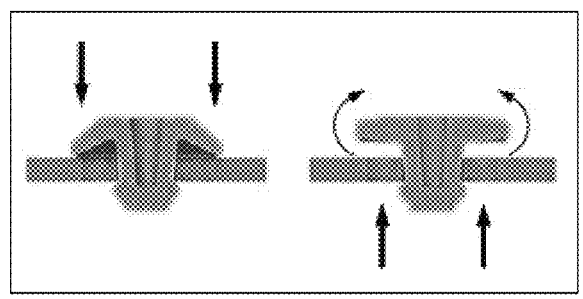
Figure 6:
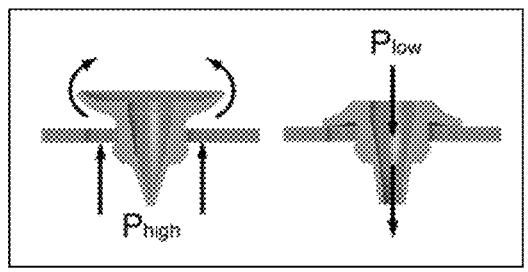
Figure 6:
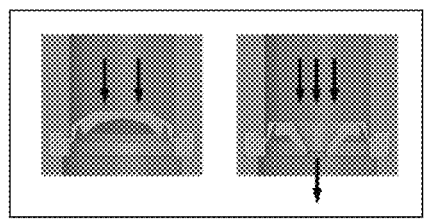
Figure 6:
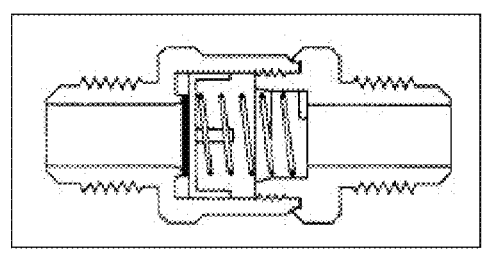

This effort included the evaluation of various off-the-shelf (OTS) or original-equipment-manufacturer (OEM) components to determine which of them could meet the pressure relief and tolerance levels required by the present invention's pressure relief component 56. Possibly suitable components include clamps and valves 56a (duckbill 56b, umbrella 56c, combination 56d, dispensing 56e, spring-force 56f, etc.), see FIG. 6. All of these are considered to come within the scope of the present invention. This approach has the advantages of utilizing existing, high volume manufacturing processes that yield lower-costs products made under precise quality control standards.

Figure 7:
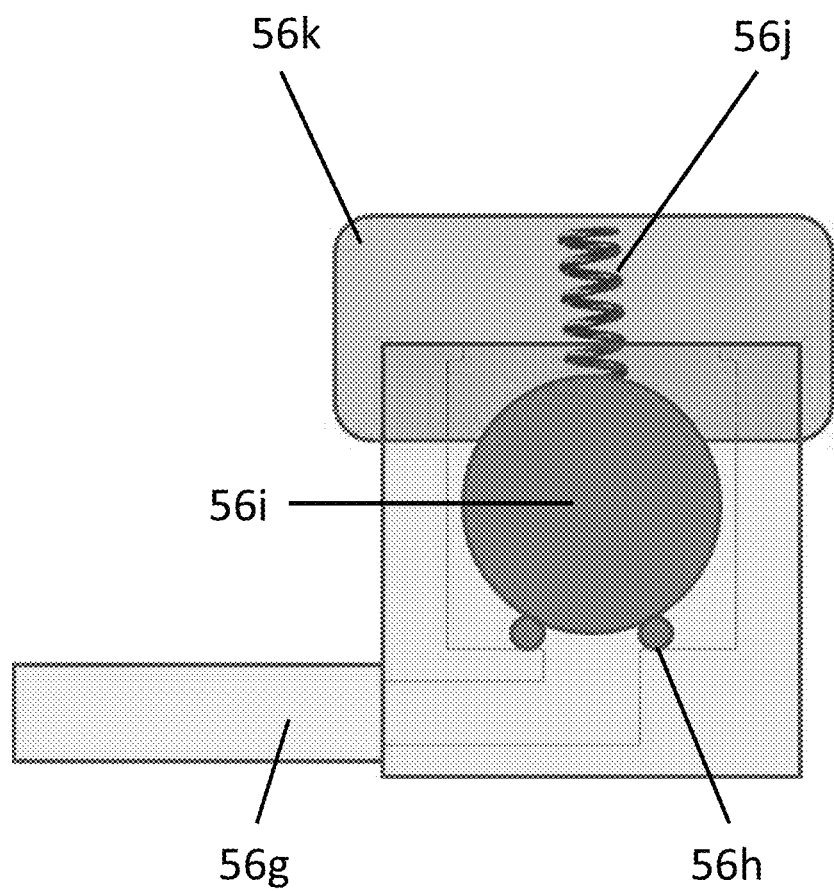
FIG. 7 illustrates a perspective view of some of the alternative components that can go into creating a custom-built version of the pressure relief component of the present invention using OTS components.

This development effort also included the assessment of a custom-built, pressure relief component 56 that utilizes only OTS components. The resulting mechanism, see FIG. 7, includes a housing 56g, O-rings 56h, a very smooth ball bearing 56i, a spring 56j, and a cap 56k. The spring applies force on the O-ring to make a fluid-tight seal in the pressure relief mechanism, and the cap can be tightened to yield specific, controlled and repeatable values of the component's relief pressures.

Other non-intuitive approaches were also followed towards the development of the required, pressure relief component 56. These included using: (a) a tube of water held at a certain height to provide a sufficient back pressure on the adapter's third opening 48c so as to prevent flow from the device until the pressure in the condom rises above this set back pressure, (b) various clamping mechanism placed on the tubing that extends from the adapter's third opening 48c, and (c) a manually operated valve and a pressure transducer and gage that has a visual readout which shows a green, red, or yellow reading that would correspond to an instruction to a health care worker who is operating this manual valve to, respectively, close, open or prepare to change the valve's position for controlling fluid flow from the device.

The only materials that the health worker needs in order to operate the present invention is possibly a condom (or other suitable expandable vessel), an adequate supply of the fluid that is used to inflate this condom and possibly a pump or other suitable means or mechanism (e.g., syringe) for causing the fluid to flow into the present invention.

It should also be noted that all of the components of the present invention, as well as the pump used to inflate the expandable vessel, are fabricated from materials that can be easily disinfected using common methods (such as soaking in a 0.05% bleach solution and flushing the device with bleach and saline); thereby, providing the present invention with the additional advantage of being reuseable. Meanwhile, the required pump can be a separate item that is to be supplied by a local health care worker or it can be incorporated into the present invention.

While the present invention has been described for use in the management of postpartum hemorrhage, it need not be limited to this application and could be used for the management of any uterine hemorrhage.

The many features and advantages of the invention should be apparent from this detailed specification, and thus, it is intended by the appended claims to cover all such features and advantages of the invention which fall within the true spirit and scope of the invention. Further, since numerous modifications and changes will readily occur to those skilled in the art, it is not desired to limit the invention to the exact construction and operation shown and described herein. Accordingly, all suitable modifications and equivalents may be resorted to, falling within the scope of the invention that is hereinafter set forth in the claims to the invention.

We claim:

1. An improved device for the management of a patient's uterine hemorrhage, wherein said device has a tube with an outer surface and a lumen that extends between the opposing ends of said tube and wherein each of said ends has an opening that connects with and allows for fluid flow through said lumen, and wherein said tube outer surface proximate an end of said tube is configured to allow for the inlet of an expandable vessel, that has an outer surface, to be connected to said tube in order to allow for said vessel to be inflated with a pump mechanism, which is supplied by a health care worker using said device, that causes fluid to flow into said tube until a portion of the expanding outer surface of said vessel expands to apply a pressure along a portion of said patient's uterine cavity in order to manage said uterine hemorrhage, the improvements to said device comprising:

wherein said expandable vessel has a configuration such that said vessel is not specifically manufactured for use with said device but is instead also to be supplied by said health care worker, and wherein said expandable vessel has proximate said inlet a coupling region that has a length greater than L, wherein said tube has two separate parts, including a larger diameter tube and a smaller diameter tube, wherein said larger diameter tube has a first and a second end and a core segment proximate said first end that has a length of L and a configuration adapted to be covered by said coupling region of said expandable vessel and used as a core and guide to assist with the placement of said expandable vessel into the uterine cavity of said patient prior to the inflation of said expandable vessel, wherein said smaller diameter tube has a first and a second end and a configuration adapted to provide said smaller diameter tube with a flexibility that enables said smaller diameter tube to be more easily managed and concealed in instances when said device is left in place within said patient for an extended period of time, a one-way, inlet valve connected to said second end of said smaller diameter tube and that has a configuration adapted to control said flow of fluid into said expandable vessel, an adapter that has a free end and first and second a connection ends and a passage that extends between said ends, and wherein said adapter has a configuration adapted to allow for said adapter first end to connect to said second end of said large diameter and for said adapter second end to connect to said first end of said smaller diameter tube, a pressure release component that has a configuration adapted to connect to said adapter free end and provide for the automatic release from said device of a quantity of fluid sufficient to maintain an approximate, steady state, uniform operating pressure of the fluid within said device, an attachment means that has a first member and a second member, wherein said first member has a configuration adapted to enable said first member to be slipped around the first end of and onto said large diameter tube and situated at a point that is substantially a distance L from said large diameter tube first end, wherein said second member has a configuration adapted to enable said second member to be slipped, after said coupling region of said expandable vessel has been placed around said large diameter tube so that the inlet of said expandable vessel lies a distance >L from said first end of said large diameter tube and said coupling region covers at least a portion of said first member, around said expandable vessel and around the first end of and onto said large diameter tube so that said second member is removably situated at a point that is approximately above said first member, and wherein said configurations of said members being further adapted so as to interact together and with said expandable vessel coupling region so as to temporarily attach said expandable vessel to said device.

2. The improved device for the management of a patient's uterine hemorrhage as recited in claim 1, wherein said pressure release component configuration is further adapted to allow for the steady state operating pressure in said device to be in the range of 0.5-4.5 psi.

3. The improved device for the management of a patient's uterine hemorrhage as recited in claim 2, wherein said pressure release component configuration is further adapted to allow for said release of fluid from said device so that the steady state operating pressure in said device is controlled to within the range of 5%-30% of said steady state operating pressure.

4. The improved device for the management of a patient's uterine hemorrhage as recited in claim 1, wherein said expandable vessel has an elasticity such that a segment of said vessel is stretchable to a length that is 500% to 800% of the original length of said section.

5. The improved device for the management of a patient's uterine hemorrhage as recited in claim 4, wherein said pressure release component configuration is further adapted to allow for said release of fluid from said device so that the steady state operating pressure in said device is controlled to within the range of 5%-30% of said steady state operating pressure.

6. The improved device for the management of a patient's uterine hemorrhage as recited in claim 5, wherein said distance, L, that said core segment of said tube extends into said expandable vessel, is in the range of 4-8 inches.

7. The improved device for the management of a patient's uterine hemorrhage as recited in claim 1, wherein said pressure release component configuration is further adapted to allow for said release of fluid from said device so that the steady state operating pressure in said device is controlled to within the range of 5%-30% of said steady state operating pressure.

8. The improved device for the management of a patient's uterine hemorrhage as recited in claim 1, wherein said distance, L, that said core segment of said tube extends into said expandable vessel, is in the range of 4-8 inches.

* * * * *